(12) United States Patent
Schultz et al.

(10) Patent No.: US 7,053,097 B1
(45) Date of Patent: May 30, 2006

(54) INHIBITORS OF GLYCOGEN SYNTHASE 3 KINASE

(75) Inventors: Peter Schultz, Oakland, CA (US); David B. Ring, Palo Alto, CA (US); Stephen D. Harrison, Berkeley, CA (US); Andrew M. Bray, Victoria (AU)

(73) Assignee: Chiron Corporation, Emeryville, CA (US)

( * ) Notice: Subject to any disclaimer, the term of this patent is extended or adjusted under 35 U.S.C. 154(b) by 1190 days.

(21) Appl. No.: 09/707,548

(22) Filed: Nov. 6, 2000

Related U.S. Application Data

(63) Continuation of application No. 08/948,887, filed on Oct. 10, 1997, now Pat. No. 6,153,618.

(60) Provisional application No. 60/028,306, filed on Oct. 11, 1996.

(51) Int. Cl.
  C07D 473/16 (2006.01)
  A61K 31/52 (2006.01)
  A61P 25/28 (2006.01)

(52) U.S. Cl. .................... 514/263.4; 544/277

(58) Field of Classification Search ........... 514/260, 514/261, 263.4; 544/273, 277
See application file for complete search history.

(56) References Cited

U.S. PATENT DOCUMENTS

| | | | |
|---|---|---|---|
| 5,837,853 A | 11/1998 | Takashima et al. | |
| 5,866,702 A | 2/1999 | Mackman et al. | |
| 6,153,618 A * | 11/2000 | Schultz | 544/277 |
| 6,767,906 B1 * | 7/2004 | Imbach et al. | 514/234.2 |

FOREIGN PATENT DOCUMENTS

| | | |
|---|---|---|
| EP | 616032 | 9/1994 |
| WO | WO 97/16452 | 5/1997 |
| WO | WO 97/22360 | 6/1997 |
| WO | WO 97/41854 | 11/1997 |
| WO | WO-97-16452 * | 5/1998 |

OTHER PUBLICATIONS

Pelech, Neurobiology of Aging vol. 16(3) 247, 1995.*
Imahori, J. Biochem. 121, 179(1997.*
Briscoe, Current Biology 5(3) 228 (1995).*
Welsh, Trends in Cell Biology 6(7) 274 (1996).*
Anderton et al., "Modulation of PHF-Like Tau Phosphorylation in Cultured Neurones and Transfected Cells," *Neurobiology of Aging* 16(3):389-402, 1995.
Borthwick et al., "Inhibition of Glycogen Synthase Kinase-3 by Insulin in Cultured Human Skeletal Muscle Myoblasts," *Biochemical and Biophysical Research Communications* 210(3):738-745, May 25, 1995.
Briscoe et al., "A Kinases for Cell-Fate Determination?" *Current Biology* 5(3):228-231, 1995.

Havlicek et al., "Cytokinin-Derived Cyclin-Dependent Kinase Inhibitors: Synthesis and cdc2 Inhibitory Activity of Olomoucine and Related Compounds," *J. Med. Chem.* 40:408-412, 1997.
Imahori et al., "Physiology and Pathology of Tau Protein Kinases in Relation to Alzheimer's Disease," *J. Biochem.* 121(2):179-188, 1997.
Klein and Melton, "A Molecular Mechanism for the Effect of Lithium on Development," *Proc. Natl. Acad. Sci. USA* 93:8455-8459, Aug. 1996.
Latimer et al., "Stimulation of MAP Kinase by v-raf Transformation of Fibroblasts Fails to Induce Hyperphosphorylation of Transfected Tau," *FEBS Letters* 365:42-46, 1995.
Lovestone et al., "Alzheimer's Disease-Like Phosphorylation of the Microtubule-Associated Protein Tau by Glycogen Synthase Kinase-3 in Transfected Mammalian Cells," *Current Biology* 4(12):1077-1086, 1994.
Massillon et al., "Identification of the Glycogenic Compound 5-Iodotubercidin as a General Protein Kinase Inhibitor," *Biochem. J.* 299:123-128, 1994.
Normon et al., "A Structure-Based Library Approach to Kinase Inhibitors," *J. Am. Chem. Soc.* 118:7430-7431, 1966.

(Continued)

*Primary Examiner*—Mark L. Berch
(74) *Attorney, Agent, or Firm*—Dennis K. Shelton; Young J. Suh; Alisa A. Harbin

(57) ABSTRACT

Compounds of formula 1:

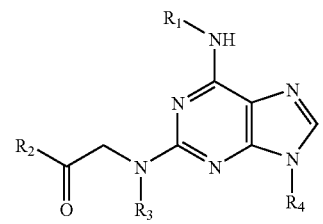

wherein
  $R_1$ is alkyl, cycloalkyl, aryl, aralkyl, heteroaryl, or heteroaralkyl, substituted with 0–3 substituents selected from lower alkyl, halo, hydroxy, lower alkoxy, amino, lower alkyl-amino, and nitro;
  $R_2$ is hydroxy, amino, or lower alkoxy;
  $R_3$ is H, lower alkyl, lower acyl, lower alkoxy-acyl, or amino-acyl;
  $R_4$ is H or lower alkyl;
and pharmaceutically acceptable salts and esters thereof; are effective inhibitors of GSK3.

10 Claims, No Drawings

OTHER PUBLICATIONS

Pelech, "Networking With Proline-Directed Protein Kinases Implicated in Tau Phosphorylation," *Neurobiology of Aging* 16(3):247-256, 1995.

Saran, "Antidiabetic Effects of Lithium," *J. Clin. Psychiatry* 43(9):383-384, Sep. 1982.

Sperber et al., "Glycogen Synthase Kinase-3β Phosphorylates Tau Protein at Multiple Sites in Intact Cells," *Neuroscience Letters* 197:149-153, 1995.

Stambolic et al., "Lithium Inhibits Glycogen Synthase Kinasae-3 Activity and Mimics Wingless Signalling in Intact Cells," *Current Biology* 6(12):1664-1668, 1996.

Sutherland et al., "Inactivation of Glycogen Synthase Kinase-3β by Phosphorylation: New Kinase Connections in Insulin and Growth-Factor Signaling," *Biochem. J.* 296:15-19, 1993.

Takashima et al., "Amyloid β Peptide Induces Cytoplasmic Accumulation of Amyloid Protein Precursor via Tau Protein Kinase I/glycogen Synthase Kinase-3β in Rat Hippocampal Neurons," *Neuroscience Letters* 198:83-86, 1995.

Takashima et al., "Exposure of Rat Hippocampal Neurons to Amyloid β Peptide (25-35) Induces the Inactivation of Phosphatidyl Inositol-3 Kinase and the Activation of Tau Protein Kinase I/glycogen Synthase Kinase-3β," *Neuroscience Letters* 203:33-36, 1996.

Takashima et al., "Tau Protein Kinase I Is Essential for Amyloid β-Protein-Induced Neurotoxicity," *Proc. Natl. Acad. Sci. USA* 90:7789-7793, Aug. 1993.

Veselý et al., "Inhibition of Cyclin-Dependent Kinases by Purine Analogs," *Eur. J. Biochem.* 224771-786, 1994.

Welsh et al., "GSK3: a SHAGGY frog story," *Trends in Cell Biology* 6(7):274-279, 1996.

* cited by examiner

INHIBITORS OF GLYCOGEN SYNTHASE 3 KINASE

CROSS-REFERENCE TO RELATED APPLICATION

This application is a continuation of prior application Ser. No. 08/948,887, now U.S. Pat. No. 6,153,618 filed Oct. 10, 1997, which in turn claims the benefit under 35 U.S.C. § 119(e) of U.S. Provisional Application Ser. No. 60/028,306, which was filed Oct. 11, 1996, and which is hereby incorporated by reference.

GOVERNMENT LICENSE RIGHTS

The U.S. Government has rights in this invention as provided for by the terms of contract No. DE-AC03-76SF00098 awarded by the Department of Energy (DOE) and by the terms of Postdoctoral Fellowships awarded by the National Science Foundation and the American Cancer Society.

DESCRIPTION

1. Field of the Invention

This invention relates generally to the field of medicinal chemistry, and specifically to compounds which inhibit the activity of glycogen synthase kinase 3 (GSK3).

2. Background of the Invention

Glycogen synthase kinase 3 (GSK3) is a proline-directed serine/threonine kinase originally identified as an activity that phosphorylates glycogen synthase, as described in Woodgett, *Trends Biochem Sci* (1991) 16:177–81. GSK3 consists of two isoforms, α and β, and is constitutively active in resting cells, inhibiting glycogen synthase by direct phosphorylation. Upon insulin activation, GSK3 is inactivated, thereby allowing the activation of glycogen synthase and possibly other insulin-dependent events. Subsequently, it has been shown that GSK3 activity is inactivated by other growth factors or hormones, that, like insulin, signal through receptor tyrosine kinases (RTKs). Examples of such signaling molecules include IGF-1 and EGF as described in Saito et al, *Biochem J* (1994) 303:27–31; Welsh et al, *Biochem J* (1993) 294:625–29; and Cross et al, *Biochem J* (1994) 303:21–26. GSK3 has been shown to phosphorylate β-catenin as described in Peifer et al, *Develop Biol* (1994) 166:543–56.

Other activities of GSK3 in a biological context include GSK3's ability to phosphorylate tau protein in vitro as described in Mandelkow and Mandelkow, *Trends in Biochem Sci* (1993) 18:480–83; Mulot et al, *FEBS Lett* (1994) 349:359–64; and Lovestone et al, *Curr Biol* (1995) 4:1077–86; and in tissue culture cells as described in Latimer et al, *FEBS Lett* (1995) 365:42–46. Phosphorylation of tau and polymerization of the phosphorylated tau is believed to allow formation of paired helical filaments that are characteristic of Alzheimer's disease. Thus, inhibition of GSK3 may be useful to treat or inhibit these disorders.

It would be advantageous to develop a method for screening for inhibitors of GSK3 for use and administration in all contexts where inhibition of GSK3 activity could have a favorable effect.

SUMMARY OF THE INVENTION

We have now invented compounds of formula 1 which inhibit the activity of GSK3:

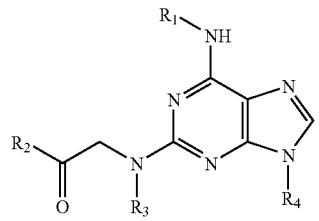

where $R_1$ is alkyl, cycloalkyl, aryl, aralkyl, heteroaryl, or heteroaralkyl, substituted with 0–3 substituents selected from lower alkyl, halo, hydroxy, lower alkoxy, amino, lower alkyl-amino, and nitro; $R_2$ is hydroxy, amino, or lower alkoxy; $R_3$ is H, lower alkyl, lower acyl, lower alkoxy-acyl, or amino-acyl; $R_4$ is H or lower alkyl; and pharmaceutically acceptable salts and esters thereof.

Another aspect of the invention is a pharmaceutical composition, comprising a compound of formula 1 and a pharmaceutically acceptable excipient.

Another aspect of the invention is a method for inhibiting GSK3, by contacting it with a compound of formula 1.

Another aspect of the invention is a method for treating an indication modulated by GSK3, comprising administering a compound of formula 1 to a subject in need thereof.

DETAILED DESCRIPTION

Definitions

The term "compound of formula 1" refers to compounds having the general structure:

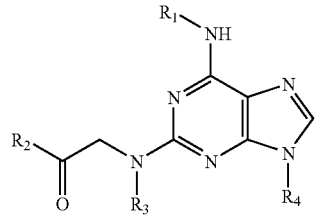

wherein
  $R_1$ is alkyl, cycloalkyl, aryl, aralkyl, heteroaryl, or heteroaralkyl, substituted with 0–3 substituents selected from lower alkyl, halo, hydroxy, lower alkoxy, amino, lower alkyl-amino, and nitro;
  $R_2$ is hydroxy, amino, or lower alkoxy;
  $R_3$ is H, lower alkyl, lower acyl, lower alkoxy-acyl, or amino-acyl;
  $R_4$ is H or lower alkyl;

and pharmaceutically acceptable salts and esters thereof.

The term "alkyl" as used herein refers to saturated hydrocarbon radicals containing from 1 to 12 carbon atoms, inclusive. Alkyl radicals may be straight or branched. Exemplary alkyl radicals include n-pentyl, n-hexyl, n-octyl, n-dodecyl, 2-dodecyl, and the like. The term "lower alkyl" as used herein refers to straight or branched chain hydrocarbon radicals having from 1 to 8 carbon atoms, such as methyl, ethyl, propyl, isopropyl, n-butyl, s-butyl, t-butyl, n-pentyl, n-hexyl, and the like. "Alkoxy" refers to radicals of the formula —OR, where R is alkyl as defined above:

"lower alkoxy" refers to alkoxy radicals wherein R is lower alkyl. "Hydroxy-lower alkyl" refers to radicals of the formula HO—R—, where R is lower alkylene of 1 to 8 carbons, and may be straight or branched. "Hydroxy-lower alkoxy" refers to radicals of the formula HO—R—O—, where R is lower alkylene of 1 to 8 carbons, and may be straight or branched. "Lower alkoxy-lower alkyl" refers to groups of the formula $R_a$O—$R_b$—, where $R_a$ and $R_b$ are each independently lower alkyl.

"Alkenyl" refers to hydrocarbon radicals of 2–20 carbon atoms having one or more double bonds. Alkenyl radicals may be straight, branched, or cyclic. Exemplary alkenyl radicals include 1-pentenyl, 3-hexenyl, 1,4-octadienyl, 3,5-diethylcyclohexenyl, and the like. "Lower alkenyl" refers to alkenyl radicals having 2–8 carbon atoms.

The term "alkynyl" refers to hydrocarbon radicals of 2–20 carbon atoms having one or more triple bonds. Alkynyl radicals may be straight, branched, or cyclic. Exemplary alkynyl radicals include 1-pentynyl, 3-hexynyl, octa-2-yn-6-enyl, 3,5-diethylcyclohexynyl, and the like. "Lower alkynyl" refers to alkynyl radicals having 2–8 carbon atoms.

The term "cycloalkyl" refers to alkyl radicals of 3–20 carbon atoms having at least one ring of carbon atoms, such as cyclopropyl, cyclobutyl, cyclopentyl, cyclohexyl, 2-methylcyclopentryl, and the like. "Bicycloalkyl" refers to alkyl radicals of 7–20 carbon atoms having at least two fused rings of carbon atoms (in which one or more carbon atoms are members of both rings). "Tricycloalkyl" refers to alkyl radicals of 7–20 carbon atoms having at least three fused rings of carbon atoms (in which one or more carbon atoms of each ring are simultaneously members of another ring).

The term "haloalkyl" refers to an alkyl radical substituted with one or more halogen atoms. Exemplary haloalkyl radicals include trifluoromethyl, 2,2,2-trifluoroethyl, 3-chlorocyclohexyl, 2-bromo-3-chlorocyclohexyl, 2,3-dibromobutyl, and the like.

The term "haloalkenyl" refers to an alkenyl radical substituted with one or more halogen atoms. Exemplary haloalkenyl radicals include 3-chloroprop-2-enyl, 4,4-dichlorobut-2-enyl, 5-bromo-3-methylcyclohex-2-enyl, and the like.

"Aryl" refers to aromatic hydrocarbons having up to 14 carbon atoms, preferably phenyl or naphthyl. "Aryl-lower alkyl" refers to radicals of the form Ar—R—, where Ar is aryl and R is lower alkyl. "Aryloxy" refers to radicals of the form Ar—O—, where Ar is aryl. "Aryloxy-lower alkyl" refers to radicals of the form ArO—R—, where Ar is aryl and R is lower alkyl.

The term "acyl" refers to a radical of the formula RCO—, in which R is H, alkyl as defined above, phenyl, benzyl or naphthyl. Exemplary acyl groups include acetyl, propionyl, formyl, t-butoxycarbonyl, benzoyl, and the like. "Lower acyl" refers to radicals wherein R is lower alkyl.

The term "halo" refers to a halogen radical, such as F, Cl, Br, or I.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of non-insulin dependent diabetes melitis (NIDDM) in a patient may be reduction in the serum levels of glucose. Treatment of Alzheimer's disease may be halting or retarding the progression of the disease (e.g., as measured by a reduction in the rate of dementia).

The term "glycogen synthase kinase 3" or "GSK3" as used herein refers to a protein originally identified by its phosphorylation of glycogen synthase as described in Woodgett et al, *Trends Biochem Sci* (1991) 16:177–81.

The term "biological condition mediated by GSK3 activity" as used herein refers to any biological or medical condition or disorder in which effective GSK3 activity is identified, whether at normal or abnormal levels. The condition or disorder may be caused by the GSK3 activity or may simply be characterized by GSK3 activity. That the condition is mediated by GSK3 activity means that some aspect of the condition can be traced to the GSK3 activity. It is expected that by the method of the invention, inhibiting the GSK3 activity will then prevent, ameliorate or treat the condition so characterized.

The term "CREB peptide" as used herein refers to a sequence within the CREB DNA-binding protein as described in Wang et al, *Anal. Biochem* (1994) 220:397–402.

General Methods and Detailed Description

The present invention provides for the inhibition of GSK3 activity, which includes, for example, inhibition of its kinase activity. By inhibiting GSK3 kinase activity, other activities downstream of GSK3 kinase activity are inhibited. For example, inhibition of the GSK3 kinase activity can result in the activation of glycogen synthase, because normally GSK3 acts constitutively in cells to inactivate glycogen synthase by direct phosphorylation. When GSK3 kinase activity is inhibited, glycogen synthase may activate leading to a cascade of events. GSK3 is also known to act as a kinase in a variety of other contexts, including but not limited to, for example, phosphorylation of c-jun, β-catenin, and tau protein. It is understood that inhibition of GSK3 kinase activity can lead to a variety of effects in a variety of biological contexts. The invention is not limited, however, by any theories of mechanism of how the invention works.

Compounds of the invention may be prepared following standard techniques. See for example, T. C. Norman et al., *J. Am. Chem. Soc.* (1996) 118:7430–31, describing the synthesis of olomoucine derivatives. Briefly, compounds may be prepared from 2-amino-6-chloropurine, available, for example, from Aldrich Chemical Co. (St. Louis, Mo.).

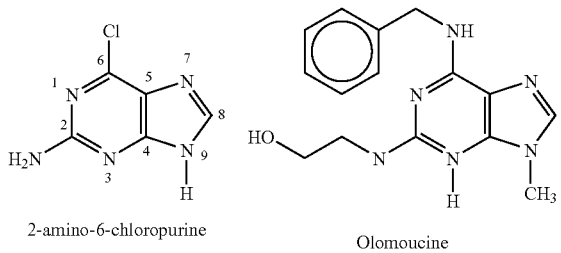

2-amino-6-chloropurine

Olomoucine

Substitutions at $R_4$ (the $N^3$ position) may be introduced by reacting the starting material with a strong base (for example NaH) and an alkyl halide (for example, $CH_3I$) in a solvent such as DMF. The $C^2$ amino group is alkylated by $S_N2$ displacement with a protected 2-haloacetic ester, for example, t-butyl α-iodoacetate, using a strong base (e.g., NaH) in an aprotic solvent such as DMF. The protecting group (e.g., t-butyl) may be converted to the $R_2$ substitution, or may be removed to allow immobilization of the compound on a solid phase for further modification. For example, one may treat the ester with trifluoroacetic acid (TFA) and 1,4-dimethoxybenzene, followed by 1 eq PyBroP, 1 eq of p-nitrophenol, and 3 eq DIEA in $CH_2Cl_2$, followed by reaction with Rink resin, 0.06 M DEA, and $CH_2Cl_2$ to provide the purine derivative coupled to a solid support.

The $R_3$ substitution may be introduced directly by alkylation (as above) or acylation with a reactive acyl halide (e.g., propionyl chloride). $R_3$ groups bearing reactive moieties may require protection, for example a terminal OH may require protection with a t-butyl group. The $C^6$ position amino group and $R^1$ substitution may then be introduced by contacting the intermediate with a reagent of the formula $R_1$—$NH_2$ (for example, 4-trifluoromethylbenzylamine) in DMF/DMSO. The resulting compound may then be cleaved from the resin, e.g., by treatment with $CH_2Cl_2$/TFA/$Me_2S$ at room temperature. The resulting compound (with $R_2$=$NH_2$) may be modified to provide other $R_2$ substitutions by standard techniques (esterification, etc.).

In presently preferred compounds of the invention, $R_1$ is either a lipophilic alkyl (such as 3-methylbutyl, pentyl, hexyl, cyclohexyl, and the like, preferably 3-methylbutyl) or a substituted benzyl or pyridylmethyl radical, especially 4-fluorobenzyl, 3-pyridylmethyl, 4-pyridylmethyl, 4-trifluoromethylbenzyl, 4-methoxybenzyl, or 4-chlorobenzyl. $R_2$ is preferably $NH_2$, and $R_4$ is preferably lower alkyl, particularly methyl. $R_3$ is preferably H or acyl, optionally substituted with $NH_2$ or $CH_3O$, especially propionyl, 2-aminoacetyl, 2-methoxyacetyl, 3-methylbutyryl, 3-methoxypropionyl, butyryl, or 3-aminopropionyl.

Compounds of the invention are assayed for activity by standard techniques, preferably employing the GSK3 assay described in the examples below. The methods include methods to assay for GSK3 kinase activity in an in vitro or cell-based assay, a method to assay for inhibitors of binding to GSK3, and an in vivo Drosophila eye screening assay.

General aspects of the kinase activity assays are conducted as described in U.S. Pat. No. 4,568,649; EP 154,734; and JP 84/52452, incorporated herein by reference, which describe kinase activity assays conducted for kinases other than GSK3. It is believed that GSK3 isoforms α and β phosphorylate serine and threonine residues in the amino acid context serine-proline (SP) or threonine-proline (TP), as well as at the N-terminal serine in the motif SXXXS, provided that the C-terminal serine in this sequence is prephosphorylated, as described in Wang et al, *Anal Biochem* (1994) 220:397–402 and Roach, *J Biol Chem* (1991) 266:14139–42.

Two of the methods for identifying specific inhibitors of GSK3 are an in vitro kinase assay and a cell-based kinase assay. Both kinase assays are performed similarly, with the distinction between them that the in vitro assay screens inhibitors that will act on the polypeptide GSK3, and the cell-based assay screens in addition for inhibitors that can act within the cell at any step in the process of expression of GSK3. Thus, the cell-based assay can screen for, for example, those inhibitors that act during transcription of GSK3 or that can act during intracellular post-transcriptional events in the process of making mature GSK3.

For the in vitro form of the assay, recombinant GSK3 is combined with the other components of the assay including a peptide substrate, and a compound of the invention. The assay published in Wang et al is a GSK3 assay makes use of a substrate peptide whose sequence is based on that of the GSK3 phosphorylation site in the CREB DNA-binding protein. In the published assay, the C-terminal serine in the SXXXS motif is prephosphorylated by casein kinase II. However, a modified peptide of motif SXXXS having an N-terminal anchor ligand can be synthesized with the C-terminal serine prephosphorylated (Chiron Mimotopes, Clayton, Australia). The substrate is then able to accomplish both binding to a substrate anchor at the N-terminal anchor ligand and to eliminate the need to phosphorylate the C-terminal serine as a separate step. The anchor ligand is a molecule or mechanism for keeping the substrate peptide present during a wash. For example, where the substrate anchor is biotin, especially in the case where the substrate is bound at the N-terminus to biotin, the anchor can be a molecule that binds biotin, for example, streptavidin.

To conduct the assay using microwells, scintillant may be present by coating the wells with a phosphorescent material, or by adding it later in a wash step. The scintillant can be purchased from Packard, Meriden, Conn. Wells coated with scintillant are then coated with streptavidin. Where the scintillant is added later in a wash step, the streptavidin can be present on agarose beads. In any event, the streptavidin in the wells binds the biotin that contacts it. Where the substrate anchor is biotin, the radiolabel on the phosphorylated substrate that has been conjugated to the biotin will cause the phosphorescent material to phosphoresce.

Where the streptavidin is attached to phosphorescent agarose beads, binding a biotin-conjugated radiolabeled peptide substrate will cause the beads to phosphoresce and will be an indication of the inhibitory activity of the candidate inhibitor. In both the case of the wells lined with the phosphorescent material, and the agarose beads, a reduction in phosphorescence as compared to a control amount of phosphorescence measured under non-inhibitory conditions, indicates the presence of a functional inhibitor of GSK3 activity. If the peptide has been phosphorylated by GSK3 with $^{32}$P-labeled or $^{33}$P-labeled phosphate, radioactive decay will cause the phosphorescent material present in a microwell or mixed in agarose beads that are present in the reaction mixture to emit light and the measure of the amount of light emitted will be a measure of the activity of GSK3 in the assay. Low activity of GSK3 observed in the presence of a candidate inhibitor, as compared to the activity of GSK3 in the absence of the inhibitor, may indicate that the inhibitor is functional and can inhibit GSK3 kinase activity. In any case, an equal amount of streptavidin should be loaded into each well or should be affixed to the agarose beads, and an equal amount of the beads added to each assay.

The cell-based assay includes in addition, a cell that can express GSK3, such as for example a cell transformed with the gene encoding GSK3, including regulatory control sequences for the expression of the gene. For conducting the cell-based assay, the cell capable of expressing GSK3 is incubated in the presence of a compound of the invention, the cell is lysed and the GSK3 is immunoprecipitated or otherwise purified, and the purified GSK3 is placed in contact with a peptide substrate, and radiolabeled phosphate-ATP. The amount of phosphorylation of the substrate is an indication of the degree of inhibition accomplished by the compound of the invention. During the cell-based assay, inhibition of GSK3 activity may occur either by inhibiting the expression of GSK3 or by inhibition of GSK3's protein kinase activity, both of which will be indicated by phosphorylation (or lack thereof) of the substrate peptide in the cell-based assay. However, one can determine which aspect is inhibited by assaying inhibition of GSK3 in vitro as described above.

An alternative assay that can be used to screen in vivo for inhibitors of GSK3 kinase activity is a Drosophila eye screen for inhibitors. The fly eye screen detects inhibitory activity by expressing GSK3 in Drosophila under the control of an eye-specific promoter. The eye specific promoter can be any promoter specific to expression of proteins in eye tissue, including but not limited to, for example, GMR as described in Hay et al, *Development* (1994) 120:2121–29, and the sevenless promoter, as described in Bowtell et al, *Genes and Development* (1988) 2:620–34. The screening assay for inhibitors of GSK3 activity is then conducted by feeding the flies food containing a compound of the invention. If the inhibitor is functional, the eye morphology reverts from mutant to wildtype. The expression of GSK3 under the control of the eye specific promoter leads to developmental defects which result in obvious aberrations in the external morphology of the external eye tissue. The mutant morphology that results in these transgenic flies is called "roughening". These defects may depend on GSK3 activity, as indicated by a control experiment using developing flies expressing a GSK3 mutant that contains a mutated kinase domain. The fly eye cells transformed with a catalytically inactive GSK3 mutant are incapable of eliciting the rough eye morphological effects of the catalytically active counterpart.

Drosophila embryos are transformed by the method of Karess and Rubin, *Cell* (1984) 38:135–46 with a polynucleotide construct comprising a GSK3 coding sequence under the regulatory control of a GMR promoter. The flies are allowed to develop normally and are selected by eye morphology for successful transformants. Successful transformants have an aberrant morphology characterized by rough eye cell morphology that is detectable under a dissecting microscope. The transgenic flies are then fed food spiked with an appropriate dose of a compound of the invention. The amount of the inhibitor will depend on the deduced possible potency of the molecule as an inhibitor. The flies are fed a compound of the invention throughout third instar larval development, during which time they are observed for reversions of their eye morphology to wildtype or normal. Positives are identified. This method may also be applied as a primary screen to identify additional compounds of the invention that have positive activity. Variations to the protocol include injecting a compound of the invention into the third instar larvae of the transformants which are then observed for a reversion of the rough eye morphology to normal.

The compounds of the invention may be administered by a variety of methods, such as intravenously, orally, intramuscularly, intraperitoneally, bronchially, intranasally, and so forth. The preferred route of administration will depend upon the nature of the compound and the condition to be treated. Compounds may be administered orally if well absorbed and not substantially degraded upon ingestion (compounds of the invention are generally resistant to proteases). The compounds may be administered as pharmaceutical compositions in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, sustained-release patches, and the like. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® minipump. Further, one may provide the compound in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

EXAMPLES

The examples presented below are provided as a further guide to the practitioner of ordinary skill in the art, and are not to be construed as limiting the invention in any way.

Example 1

Preparation of Compounds

Compounds of the invention were prepared following the method disclosed in T. C. Norman et al., *J. Am. Chem. Soc.* (1996) 118:7430–31.

(A) 2-Amino-6-chloropurine was treated with NaH (1.1 eq) and $CH_3I$ (1 eq) in DMF. The product was treated with trifluoroacetic anhydride (3 eq) in $CH_2Cl_2$, then alkylated with t-butyl α-iodoacetate (2 eq) and NaH (1.1 eq) in DMF. The reaction was quenched with $K_2CO_3$ in MeOH. The product was then treated with trifluoroacetic acid (TFA) and 1,4-dimethoxybenzene, followed by PyBroP (1 eq), p-nitrophenol (1 eq), and DIEA (3 eq) in $CH_2Cl_2$, and coupled to Rink-derivatized polyethylene crowns (Chiron Mimotopes, Clayton, Australia), 0.06 M DIEA, and $CH_2Cl_2$ to provide the purine derivative coupled to a solid support ($R_4$=methyl).

The intermediate was acylated with 2-methoxyacetyl chloride (0.2 M) in the presence of 4-methyl-2,6-di-t-butylpyridine (0.25 M) in $CH_2Cl_2$ at 37° C. for 12 hours ($R_2$=$CH_3OCH_2CO$). The resulting intermediate was reacted with 4-trifluoromethyl-benzylamine (0.25 M) in DMF/DMSO (1:1 by volume) at 4° C. for 16 h, followed by cleavage from the support by treatment with $CH_2Cl_2$/TFA/$Me_2S$ at room temperature for 2 hours, to provide CHIR 21208:

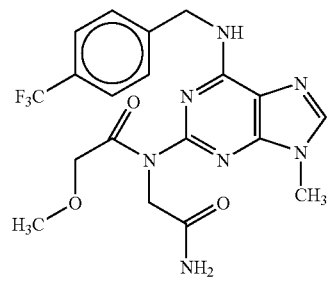

(B) Proceeding as in part (A) above, the following compounds were made:

| Compound ID | $R_1$ | $R_2$ | $R_3$ | $R_4$ |
|---|---|---|---|---|
| 21172 | $F_3C$-φ-$CH_2$—(*) | $NH_2$ | H | $CH_3$ |
| 21232 | $F_3C$-φ-$CH_2$— | $NH_2$ | $NH_2CH_2CO$— | $CH_3$ |
| 21220 | $F_3C$-φ-$CH_2$— | $NH_2$ | $CH_3CH_2CO$— | $CH_3$ |
| 20957 | 2-pyridylmethyl | $NH_2$ | H | $CH_3$ |
| 20981 | 2-pyridylmethyl | $NH_2$ | $(CH_3)_2CHCH_2CO$ | $CH_3$ |

-continued

| Compound ID | R₁ | R₂ | R₃ | R₄ |
|---|---|---|---|---|
| 21005 | 2-pyridylmethyl | NH₂ | CH₃CH₂CO— | CH₃ |
| 21132 | (CH₃)₂CHCH₂CH₂ | NH₂ | CH₃OCH₂CO | CH₃ |
| 21131 | 4-F-φ-CH₂— | NH₂ | CH₃OCH₂CO | CH₃ |
| 21196 | F₃C-φ-CH₂— | NH₂ | (CH₃)₂CHCH₂CO | CH₃ |
| 21095 | 4-F-φ-CH₂— | NH₂ | H | CH₃ |
| 21100 | 4-CH₃O-φ-CH₂ | NH₂ | H | CH₃ |
| 20951 | cyclohexyl | NH₂ | H | CH₃ |
| 20956 | 4-pyridylmethyl | NH₂ | H | CH₃ |
| 21004 | 4-pyridylmethyl | NH₂ | CH₃(CH₂)₂CO | CH₃ |
| 21075 | 4-Cl-φ-CH₂ | NH₂ | CH₃(CH₂)₂CO | CH₃ |
| 21156 | (CH₃)₂CH(CH₂)₂ | NH₂ | NH₂(CH₂)₂CO | CH₃ |

(*)φ = phenyl

Example 2

Assay (A) A GSK3β gene was created in which a haemagluttinin (HA) epitope was fused to the N-terminal end of the GSK3β open reading frame in plasmid vector pCG, a pEVRF derivative, described in Giese et al. *Genes &Development* (1995) 9:995–1008, and in Matthias et al., *Nucleic Acids Res.* (1989) 17:6418. pCG has a modified polylinker, and directs expression in mammalian cells from the human cytomegalovirus promoter/enhancer region. The resulting plasmid is pCG-HA-GSK3β. pCG-HA-GSK3β was transiently transfected into COS cells on 10 cm tissue culture plates using DEAE-Dextran, as described in Ausubel et al (1994) "Current Protocols In Molecular Biology", (Greene Publishing Associates and John Wiley & Sons, New York, N.Y.).

The final density of cells was 70% confluent and these cells were lysed in 700 μl Triton lysis buffer (20 mM Tris HCl, pH 7.9, 137 mM NaCl, 1.0% Triton® X-100, 10% glycerol, 1 mM NaVO₃, 20 mM NaF, 30 mM pNpp, 15 mM PPi). Anti-HA antibody (12CA5 monoclonal antibody purchased from Boehringer Mannheim, Indianapolis, Ind.) was added to 300 μl of this lysate to a final concentration of 4 μg/ml and incubated for 1 h at 4° C. 100 μl of a 50% slurry of protein A-Sepharose® beads were added for 2 h at 4° C.

The beads were pelleted by centrifugation for 10 seconds in a microcentrifuge and washed with 0.5 M LiCl, 0.5% Triton® X-100, twice with phosphate buffered saline (PBS) and once with 10 mM Tris HCl, pH 7.5, 5 mM MgCl₂, 1 mM DTT. All wash buffers contained 1 mM NaVO₃ and 25 mM β-glycerolphosphate. 33 μl of the beads were analyzed by SDS-PAGE and western blotting with anti-HA antibody (12CA5) to quantitate the amount of HA-GSK3β present.

The remaining 17 μl of beads was assayed according to the protocol of Wang et al, *Anal Biochem* (1994) 220: 397–402. To each 17 μl of pellet was added 3 μl 10× GSK buffer (100 mM MgCl₂, 20 mM DTT, 3M Tris HCl, pH 7.5), 0.7 μl CREB peptide (either prephosphorylated or non-prephosphorylated, 5 mg/ml, Chiron Mimotopes Peptide Systems, San Diego, Calif.), 0.3 μl 10 mM rATP, 1 μl γ³²P-ATP (6000 Ci/mmol), 0.06 μl 5 mg/ml of protein kinase inhibitor (a protein kinase-A inhibitor or PKI), and 25 μl H₂O. The reaction was allowed to proceed for 20 min at 22° C. and then was stopped with 8 μl 500 mM EDTA. 22 μl of each reaction was spotted onto P81 phosphocellulose filter paper (purchased from Gibco-BRL Life Technologies, Gaithersburg, Md.) washed 4 times for 5 minutes in 75 mM H₃PO₄ The filter papers were then assayed in a scintillation counter. Filter papers from experiments using the prephosphorylated CREB peptide substrate yielded counts of 85,000±5,000 cpm/min, whereas filter papers from experiments using the non-prephosphorylated CREB peptide substrate yielded counts of 5,000±1,000 cpm/min. The results indicated that the substrate was phosphorylated by GSK3 in the absence of an inhibitor, although the control substrate was not phosphorylated. This experiment demonstrates the specificity of the peptide as a GSK3 substrate.

(B) The compounds prepared in Example 1 above were assayed for activity as follows:

A 96-well round bottom plate was blocked by incubation with 400 μl/well 1% BSA/PBS for 60 min at room temperature. The blocking reagent was then aspirated. An enzyme/substrate buffer was prepared (1.225 ml 1M Tris-HCl, pH 7.5, 0.41 ml 1M MgCl₂, 41 μl DTT, 250 μl 500 μg/ml GSK-3β, 9.5 μl 5 mg/ml biotin-phosphopeptide, 33.1 ml 1% BSA/PBS), and 300 μl enzyme/substrate/buffer was added to each well.

Varying concentrations of each compound were added to individual wells, or staurosporine in DMSO (final concentrations of staurosporine 100 nM or 20 nM). Next 50 μl/well ATP mixture (3.85 μl 10 mM cold ATP, 8 μl hot ATP, 5.5 ml H₂O) was added, and the reaction allowed to proceed for 180 min at room temperature.

Three streptavidin-coated Labsystems Combiplate 8 plates were blocked with 1% BSA/PBS, 300 μl/well, for ≧60 min at room temperature, and the blocking reagent aspirated. Stopping reagent (50 μM ATP, 20 mM EDTA) (100 μl/well) was added to the streptavidin-coated plates, and 100 μl of the enzyme reaction mixture transferred to the streptavidin-coated plates in triplicate. The plates were incubated at room temperature for 60 min, and washed 5× with PBS using a Corning plate washer. Finally, Microscint-20 scintillation fluid (200 μl/well) was added to the plates, the plates sealed, and after incubating for 30 min, counted on a TopCount counter. The results were as follows:

| Compound | % inhibition at 1 μM |
|---|---|
| 21208 | 63 |
| 21172 | 61 |
| 21232 | 58 |
| 21220 | 53 |
| 20957 | 50 |
| 20981 | 47 |
| 21005 | 45 |
| 21132 | 45 |
| 21131 | 43 |
| 21196 | 43 |
| 21095 | 41 |
| 21100 | 41 |
| 20951 | 40 |
| 20956 | 40 |
| 21004 | 40 |
| 21075 | 40 |
| 21156 | 40 |

The results demonstrated that the compounds of the invention were effective in inhibiting the kinase activity of GSK3.

What is claimed:
1. A compound of formula 1:

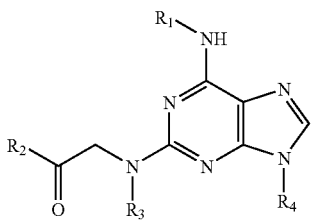

wherein:
$R_1$ is aryl, substituted with 0–3 substituents selected from lower alkyl, halo, hydroxy, lower alkoxy, amino, lower alkyl-amino, and nitro;
$R_2$ is hydroxy, amino, or lower alkoxy;
$R_3$ is H, lower acyl, lower alkoxy-acyl, or amino-acyl;
$R_4$ is H or lower alkyl;
and pharmaceutically acceptable salts thereof.
2. The compound of claim 1 wherein $R_4$ is methyl.
3. The compound of claim 2, wherein $R_2$ is amino.
4. A pharmaceutical composition, comprising: a compound of the formula 1:

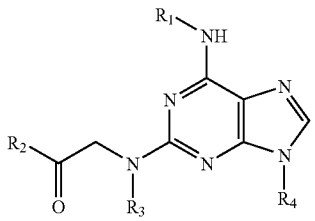

wherein
$R_1$ is aryl, substituted with 0–3 substituents selected from lower alkyl, halo, hydroxy, lower alkoxy, amino, lower alkyl-amino, and nitro;
$R_2$ is hydroxy, amino, or lower alkoxy;
$R_3$ is H, lower acyl, lower alkoxy-acyl, or amino-acyl;
$R_4$ is H or lower alkyl;
or a pharmaceutically acceptable salt thereof; and a pharmaceutically acceptable excipient.
5. The compound of claim 3, wherein $R_3$ is propanoyl.
6. The compound of claim 3, wherein $R_3$ is 3-methylbutanoyl.
7. The compound of claim 3, wherein $R_3$ is butanoyl.
8. The compound of claim 3, wherein $R_3$ is H.
9. The compound of claim 3, wherein $R_3$ is aminoacetyl.
10. The compound of claim 3, wherein $R_3$ is methoxyacetyl.

* * * * *